United States Patent
Kay

(10) Patent No.: US 7,977,500 B2
(45) Date of Patent: Jul. 12, 2011

(54) PLATINUM COMPLEXES FOR TARGETED DRUG DELIVERY

(75) Inventor: Heidi Kay, Springfield, VA (US)

(73) Assignee: University of South Florida, Tampa, FL (US)

( * ) Notice: Subject to any disclaimer, the term of this patent is extended or adjusted under 35 U.S.C. 154(b) by 658 days.

(21) Appl. No.: 11/667,617

(22) PCT Filed: Nov. 10, 2005
(Under 37 CFR 1.47)

(86) PCT No.: PCT/US2005/041129
§ 371 (c)(1),
(2), (4) Date: Apr. 30, 2008

(87) PCT Pub. No.: WO2007/008247
PCT Pub. Date: Jan. 18, 2007

(65) Prior Publication Data
US 2009/0214626 A1    Aug. 27, 2009

Related U.S. Application Data

(60) Provisional application No. 60/626,730, filed on Nov. 10, 2004.

(51) Int. Cl.
*C07F 15/00* (2006.01)
(52) U.S. Cl. ...... 556/137; 514/492; 548/108; 548/304.1
(58) Field of Classification Search .................. 548/108, 548/304.1; 556/137; 514/492
See application file for complete search history.

(56) References Cited

U.S. PATENT DOCUMENTS

| | | | |
|---|---|---|---|
| 3,904,663 A | 9/1975 | Tobe et al. | |
| 4,177,263 A | 12/1979 | Rosenberg et al. | |
| 5,648,384 A | 7/1997 | Kidani et al. | |
| 5,714,327 A | 2/1998 | Houthoff et al. | |
| 5,849,790 A | 12/1998 | Palmer et al. | |
| 5,902,826 A | 5/1999 | Mogi et al. | |
| 5,998,648 A | 12/1999 | Sohn et al. | |
| 6,503,943 B1 | 1/2003 | Zak et al. | |
| 7,128,893 B2 | 10/2006 | Leamon et al. | |
| 7,166,733 B2 | 1/2007 | Nowotnik et al. | |
| 7,238,372 B2 | 7/2007 | Turkson et al. | |
| 7,566,798 B2 | 7/2009 | Kay et al. | |
| 7,754,684 B2 * | 7/2010 | Stewart et al. | 514/6 |
| 7,759,510 B2 | 7/2010 | Kay et al. | |
| 7,763,585 B2 | 7/2010 | Turkson et al. | |
| 2004/0175387 A1 | 9/2004 | Sood et al. | |
| 2005/0220754 A1 | 10/2005 | Russell-Jones et al. | |
| 2005/0288365 A1 | 12/2005 | Kay et al. | |
| 2006/0127310 A1 | 6/2006 | Russell-Jones et al. | |

FOREIGN PATENT DOCUMENTS

| | | |
|---|---|---|
| JP | H08-176175 A2 | 7/1996 |
| WO | WO 96/26949 A1 | 9/1996 |
| WO | WO 2005/016946 | 2/2005 |
| WO | WO 2005/023824 | 3/2005 |

OTHER PUBLICATIONS

Kortepeter et al., Emerging Infectious Diseases, vol. 14, No. 6, pp. 881-887 (2008).*
Heetebrij, R. J. et al., "Platinum (II)-Based Coordination Compounds as Nucleic Acid Labeling Reagents: Synthesis, Reactivity, and Applications in Hybridization Assays" *Chem Bio Chem*, 2003, pp. 573-583, vol. 4.
Cleare, M.J. and Hoeschele, J.D. "Anti-tumour platinum compounds. Relationship between structure and activity" *Platinum Metals Rev.*, 1973, 17(1):2-13.
Samatov et al. Izvestiya Akademii Nauk SSSR Seriya Khimicheskaya, 1974, pp. 1467-1472, No. 9.
Chernyaev et al. Zhurnal Neorganicheskoi Khimii, 1966, pp. 1365-1373, vol. 11.
Muraveiskaya et al. Zhurnal Neorganicheskoi Khimii, 1971, pp. 1643-1649, vol. 16.
Rudyi et al. Koordinatsionnaya Khimiya, 1975, p. 1572. vol. 1.
Muravenskaya et al. Koordinatsionnaya Khimiya, 1975, pp. 779-790. vol. 1.
Le Postollec "Spectres de vibration et struture de composes de coordination nitres du platine IV" *Journal de La Chimie Physique et de Physico-Chime Biologique*, 1965, pp, 67-72, vol. 62.
Samatov et al. Izvestiya Akademii Nauk SSSR, Seriya Khimicheskaya, 1974, pp. 2142-2144.
Chernyaev, I.I. et al. "Nitrosation of amines in platinum (IV) triamines of ribbed structure" *Zhumal Neorganicheskol Khimil*, 1967, pp. 1877-1885, vol. 12, No. 7.
Adrianova, O.N. et al. "Anomaly of the acid properties of platinum cis-dinitrotriamines of meridonal structure" *Zhurnal Neorganicheskoi Khimii*, 1978, pp. 2155-2158, vol. 23, No. 8.
Howell, B.A. et at. "Substituted catecholato(1,2-diaminocyclohexane) platinum(II) compounds" *Inorganica Chimica Acta*, 1988, pp. 181-183, vol. 142, No. 2.
Bromberg, J. "Stat proteins and oncogenesis" *J. Clin. Invest.*, 2002, pp. 1139-1142, vol. 109.
Leamon, C.P. et al. "Folate-mediated targeting: from diagnostics to drug and gene delivery" *DDT*, Jan. 2001, pp. 44-51, vol. 6, No. 1.
Lu, Y. et al. "Folate receptor-targeted immunotherapy of cancer: mechanism and therapeutic potential" *Advanced Drug Delivery Reviews*, 2004, pp. 1161-1176, vol. 56.
Russel-Jones, G. et at. "Vitamin-mediated targeting as a potential mechanism to increase drug uptake by tumours" *Journal of Inorganic Biochemistry*, pp. 1625-1633, vol. 98, (2004).
Schechter, B. et al. "Polymers in drug delivery: Immunotargeting of carrier-supported *cis*-platinum complexes" *Reactive Polymers*, pp. 167-175, vol. 25. (1995).
Walker, R. et al. "Biotinylation facilitates the uptake of large peptides by *escherichia coli* and other gram-negative bacteria" *Applied and Environmental Microbiology*, Apr. 2005, pp. 1850-1855, vol. 71, No. 4.

* cited by examiner

*Primary Examiner* — Porfirio Nazario Gonzalez
(74) *Attorney, Agent, or Firm* — Saliwanchik, Lloyd & Eisenschenk

(57) ABSTRACT

The subject invention concerns biotin-conjugated platinum complexes that exhibit direct and indirect (immunological) antitumor cell activity. The subject invention also concerns the biotin-platinum complexes of the invention that have another molecule, such as an antibody, a ligand, a receptor, etc., bound to the biotin moiety. The subject invention also concerns the use of platinum complexes of the invention to treat oncological and inflammatory disorders. The platinum complexes of the invention can also be used to treat or prevent infection by a virus or a bacterial or parasitic organism in vivo or in vitro.

41 Claims, No Drawings

PLATINUM COMPLEXES FOR TARGETED DRUG DELIVERY

CROSS-REFERENCE TO RELATED APPLICATION

This application is the U.S. national stage application of International patent application No. PCT/US2005/041129, filed Nov. 10, 2005, which claims the benefit of U.S. Provisional Application Ser. No. 60/626,730, filed Nov. 10, 2004, which is hereby incorporated by reference herein in its entirety, including any figures, tables, and drawings.

BACKGROUND OF THE INVENTION

Platinum complexes, the prototype being cisplatin (Cis-Pt), have been widely used as active anticancer agents (Ardizzoni et al., 1999; Nitiss, 2002) in a variety of human tumors, including testicular, ovarian, bladder carcinoma, head and neck, and non-small cell lung cancers. The outcome of treatments with cisplatin and other platinum-containing complexes has been strongly linked to their alkylating effects on DNA. However, the potential impact of platinum-complex-based therapy on cellular signaling and the therapeutic importance of such interactions have yet to be explored. Reports show that cisplatin induces activation of members of the mitogen-activated protein kinase (MAPK) pathways (Persons et al., 1999; Sanchez-Perez et al., 1998), which may influence drug-induced apoptosis.

Cellular responses to growth factors and cytokines are characterized by activation of the Signal Transducer and Activator of Transcription (STAT) family of cytoplasmic transcription factors (Darnell, 1997; Darnell et al., 1994; Schindler et al., 1995; Stark et al., 1998; Smithgall et al., 2000; Akira, 2000; Hirano et al., 2000; Bromberg et al., 1996; Fukada et al., 1996; Kotenko et al., 2000). STATs are activated at a very early stage involving protein tyrosine kinase phosphorylation of tyrosine associated with growth factor receptors, receptor-associated Janus kinase (Jaks) or Src kinase families. This in turn induces phosphotyrosine (pTyr)-SH2 interactions between two STAT monomers in the formation of dimers, translocation to the nucleus, and binding to specific DNA response elements regulating gene expression essential for cell proliferation, differentiation, development and survival.

Normal STAT activation is tightly-regulated and has a short duration, which is in keeping with normal cellular requirements for mounting a response to external stimuli. However, persistent activation of specific STAT proteins, particularly Stat3 and Stat5, occurs with high frequency in some tumors and has a causal role in malignant transformation by promoting growth and survival of transformed and tumorous cells, including those breast, prostate, head and neck squamous carcinoma cells, lymphomas and leukemias (Bromberg et al., 1999; Turkson et al., 1998; Bromberg et al., 1998; Catlett-Falcone et al, 1999a; Garcia et al, 2001; Grandis et al, 2000; Grandis et al., 1998; Nielsen et al., 1997; Nielsen et al, 1999; Epling-Burnette et al, 2001; reviewed in Bowman et al, 2000; Turkson et al, 2000; Song et al, 2000; Coffer et al, 2000; Lin et al, 2000; Catleff-Falcone et al, 1999b; Garcia et al, 1998). Of clinical importance, blockade of aberrant Stat3 signaling in malignant cells and whole tumors that contain them induces apoptosis and tumor regression.

BRIEF SUMMARY OF THE INVENTION

The subject invention concerns biotin-conjugated platinum complexes and uses thereof. The subject invention also concerns the biotin-platinum complexes of the invention that have another molecule, such as an antibody, a ligand, a receptor, etc., bound to the biotin moiety. The platinum complexes of the invention can be used to treat oncological, viral, bacterial, immunological, inflammatory, cardiological, neurological, and parasitic disease conditions.

DETAILED DISCLOSURE OF THE INVENTION

The subject invention concerns biotin-conjugated platinum complexes and uses thereof. Biotin is an axial ligand of the platinum complexes of the invention. A biotin-containing molecule can be conjugated to a platinum complex as described herein. Biotin is expected to form a metal-covalent bond to the Pt atom of the complex via the sulfur atom of biotin. The subject invention also concerns the biotin-platinum complexes of the invention that have a second molecule, such as an antibody, a ligand, a receptor, etc., having binding specificity for another molecule bound to the biotin moiety. In this way, a biotin-platinum complex of the invention is targeted for delivery to a site through covalent linkage to a molecule (e.g., an antibody or protein) having a binding specificity for a target moiety, such as a receptor, cell, protein, etc. The molecule can be directly conjugated to the biotin moiety, as by a covalent bond, or it can be bound via an avidin-biotin linkage where the molecule is conjugated with avidin, or a derivative thereof such as streptavidin. Platinum complexes of the invention can induce apoptosis and/or inhibit telomerase activity and/or inhibit tumor cell growth and/or target immune cells (such as macrophages or T cells) and can also be used to target cancers since the biotin content of cancerous tissue is higher than normal tissue (Merck, tenth edition). Richest sources include pancreas and liver, which may benefit targeting to these tissues. The platinum complexes of the invention also can be used as antiviral, antibacterial, and antiparasitic agents. For antibacterial or antifungal use, a molecule that binds specifically to a bacterial or fungal antigen or protein is utilized with a biotin platinum complex of the invention. It has been suggested that cellular cytotoxicity of platinum (IV) complexes is a result of platinum (IV) complexes being reduced to platinum (II) in the cell. Surprisingly, platinum (IV) complexes of the present invention may not require this type of reduction in the cells to have a cytotoxic effect. Therefore, the platinum complexes of the present invention are distinct from platinum complexes in the art by maintaining their correct oxidative conformation as platinum (IV) complexes, which are more effective and less toxic than the existing platinum (II) complexes. In addition, certain platinum complexes of the invention can also produce or induce production of free radical nitric oxide in cells thereby killing cells through the formation of free radicals.

Platinum complexes of the invention include those complexes having the structure shown in formula I or II:

(I)

(II)

wherein
X and Y are, independently, any halogen, —NO₂, —ONO, or the structure:

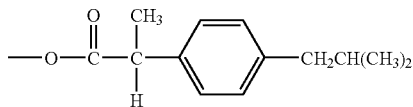

or X and Y together form the structure:

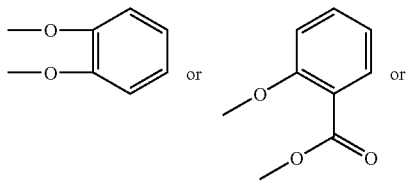

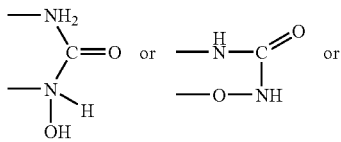

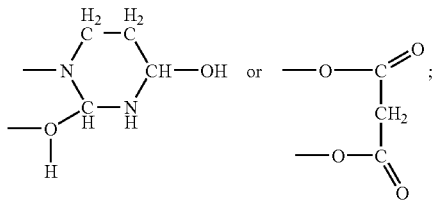

$R^1$ is —NO₂, —ONO, —OH, Cl, Br, I, or F;

$R^2$ is a biotin-containing molecule;

$R^3$ is, independently, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —NO₂, —NH₂, —NH₃, —NHR⁷, NH₂R⁷, —NH(R⁷)₂, —N(R⁷)₃, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; and $R^7$ is H, $C_{1-6}$ alkyl, alkoxy, or aryl, any of which can be optionally substituted with any halogen, —NO₂, or —COOH;

or a pharmaceutically acceptable salt thereof.

In one embodiment, X and Y can be, independently, fluoride (F⁻), chloride (Cl⁻), bromide (Br⁻) or iodide (I⁻). In a specific embodiment, X and Y are both Cl. In yet another specific embodiment, X and Y are both Br.

In one embodiment, $R^1$ is —NO₂, $R^2$ is biotin or biotin-lysine, and $R^3$ is —NH₃.

Platinum complexes of the invention can also have the structure shown in formula III:

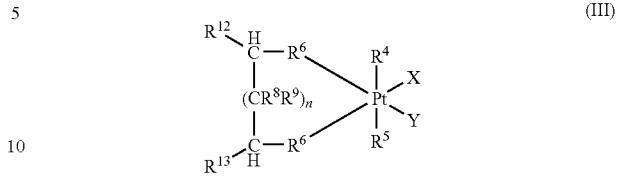

(III)

wherein
X and Y are, independently, any halogen, or the structure:

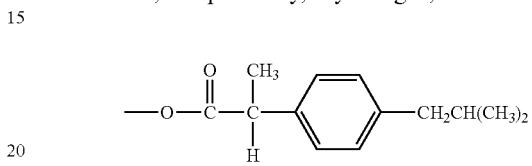

or X and Y together form the structure:

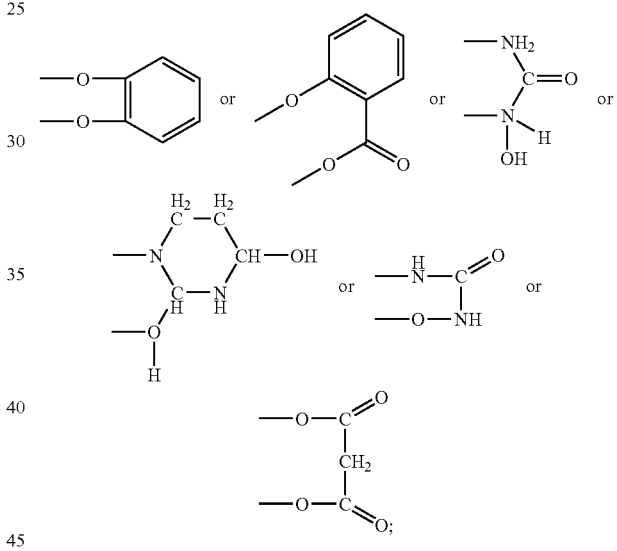

$R^4$ is —NO₂, —ONO, —OH, Cl, Br, or F;

$R^5$ is a biotin-containing molecule;

$R^6$ is, independently, NH₂, NH, NHR⁷, N(R⁷)₂, NHR⁸, N(R⁸)₂, NHR⁹, N(R⁹)₂, or NR⁸R⁹;

$R^7$ is H, $C_{1-6}$ alkyl, alkoxy, or aryl, any of which can be optionally substituted with any halogen, —NO₂ or —COOH;

$R^8$ and $R^9$ are, independently, H, $C_{1-6}$ alkyl, or —OH, any of which can be optionally substituted with any halogen, —COOH, —OH, —NO₂, —NH₂, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{12}$ and $R^{13}$ are, independently, H or $C_{1-6}$ alkyl, or $R^{12}$ and $R^{13}$ together form an aryl, cycloalkyl, heterocycloalkyl, or heteroaryl, any of which can be optionally substituted with any halogen, —COOH, —OH, —NO₂, —NH₂, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; and n is any integer from 0 to 6;

or a pharmaceutically acceptable salt thereof.

In one embodiment, X and Y can be, independently, fluoride ($F^-$), chloride ($Cl^-$), bromide ($Br^-$) or iodide ($I^-$). In a specific embodiment, X and Y are both Cl. In yet another specific embodiment, X and Y are both Br.

In one embodiment, $R^4$ is $-NO_2$, $R^5$ is biotin or biotin-lysine, $R^6$ is $-NH_2$, and n is 0.

Platinum complexes of the invention also include those complexes having the structure shown in formula VA, VB, or IV:

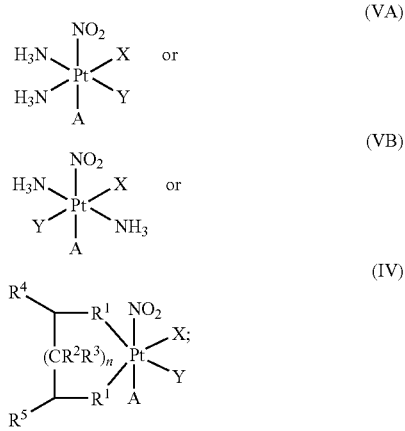

wherein

X and Y are, independently, any halogen, $-OH$, $H_2O$, or $-SO(CH_3)_2$;

or X and Y together form the structure:

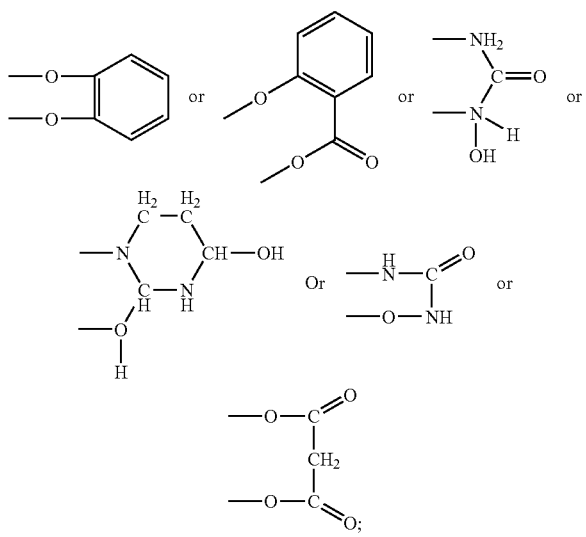

and A is a biotin-containing molecule;

and wherein $R^1$ is, independently, $NH_2$, NH, $NR^4$, $NHR^4$, $N(R^4)_2$, $NR^5$, $NHR^5$, $N(R^5)_2$, or $NR^4R^5$;

$R^2$ and $R^3$ are, independently, H, $-OH$, $C_{1-6}$ alkyl, alkoxy, cycloalkyl, aryloxy, cycloalkoxy, aryl, heteroalkyl, heterocycloalkyl, heteroaryl, arylcarbonyl, or heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl.

$R^4$ and $R^5$ are, independently, H, $C_{1-6}$ alkyl, alkoxy, cycloalkyl, aryloxy, cycloalkoxy, aryl, heteroalkyl, heterocycloalkyl, heteroaryl, arylcarbonyl, or heteroarylcarbonyl or $R^4$ and $R^5$ together form a cycloalkyl, cycloalkoxy, aryl, aryloxy, heterocycloalkyl, heteroaryl, arylcarbonyl, and heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl; and n is any integer from 0 to 6;

or a pharmaceutically acceptable salt thereof.

In one embodiment, X and Y can be, independently, fluoride ($F^-$) chloride ($Cl^-$), bromide ($Br^-$) or iodide ($I^-$). In a specific embodiment, X is Cl and Y is Cl.

Table 1 herein shows specific examples of biotin-conjugated platinum complexes contemplated within the scope of the invention.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms. For example, $C_{1-6}$ alkyl means straight or branched chain alkyl groups containing from 1 up to 6 carbon atoms. Alkoxy means an alkyl-O— group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O— group in which cycloalkyl is as defined herein. Aryl means an aromatic monocyclic or multicyclic carbocyclic ring system, including fused and spiro rings, containing from about six to about 14 carbon atoms. Aryloxy means an aryl-O-group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO— group in which the aryl group is as described herein. Heteroarylcarbonyl means a heteroaryl-CO— group in which the heteroaryl group is as described herein and heterocycloalkylcarbonyl means a heterocycloalkyl-CO— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), bromine (Br), and iodine (I).

The term pharmaceutically-acceptable salts means salts of the platinum complexes of the invention which are prepared as acids or bases, depending on the particular substituents present on the subject complexes described herein. Examples of a pharmaceutically-acceptable base addition salts include sodium, potassium, calcium, ammonium, or magnesium salt. Examples of pharmaceutically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically-acceptable salts of platinum complexes of the invention can be prepared using conventional techniques.

It will be appreciated by those skilled in the art that certain of the platinum complexes of the invention may contain one or more asymmetrically substituted carbon atoms which can give rise to stereoisomers. All such stereoisomers, including enantiomers, and diastereoisomers and mixtures, including racemic mixtures thereof, are contemplated within the scope of the present invention.

Any protein moiety that can bind in a specific manner to a target moiety present on or in a cancer cell or other cell targeted for contact or exposure to a platinum complex of the invention can be used with the present invention. In one embodiment, the protein moiety is an antibody that binds to an antigen or marker preferentially expressed on a transformed or cancerous cell. In a specific embodiment, the antibody binds to a tumor-associated marker or a tumor-specific antigen. Tumor-associated markers and tumor-specific antigens include, for example, prostate-specific antigen (PSA), prostatic acid phosphatase (PAP), cancer antigen (CA) 125, carcinoembryonic antigen (CEA), alpha-fetoprotein (AFP), CA 19-9, CA 15-3, CA 27-29, and neuron-specific enolase (NSE). Examples of antibodies/proteins that can be conjugated to biotin, or that can be labeled with avidin, or a biotin-binding derivative of avidin, and subsequently bound to a biotin-platinum complex of the invention include, but are not limited to, anti-VEGF antibody (cancers); anti-CD14 antibody (macrophages); anti-CD15 antibody (Hodgkins, T-cell lymphomas, leukemias); interferon-inducible T cell chemoattractant; anti-c-Myc antibody (cancers); anti-melanin antibody (melanoma); anti-CD20 antibody (lymphoma), anti-CD33 antibody (leukemia); anti-Her2 antibody (cancer); and anti-EGFR antibody (cancer). The protein moiety can be directly conjugated to biotin or a biotin-containing or biotin-related molecule using standard chemical materials and methods. Alternatively, the protein moiety can be conjugated with avidin or a derivative or analog thereof (e.g., streptavidin) that can bind to biotin.

Antibodies contemplated within the scope of the invention include both polyclonal and monoclonal antibodies. Preferably, the antibody is a monoclonal antibody, or an antigen binding fragment thereof. Antigen binding fragments include, but are not limited to, F(ab')$_2$, Fab', Fab, and Fv, and can be prepared using standard methods known in the art. The antibody can be derived from any animal capable of producing antibodies to a target antigen or epitope, and include, for example, primate, mouse, rat, goat, sheep, pig, and cow. Preferably, if the antibody biotin platinum complex is to be administered to humans, the antibody is a human antibody or is a "humanized" antibody derived from a non-human animal. Methods for humanizing non-human antibodies are known in the art and have been described in U.S. Pat. Nos. 5,530,101; 5,585,089; 5,693,762; 6,180,370; and 6,407,213. Antibodies of the invention can be prepared using standard techniques known in the art or can be obtained from commercial sources. Monoclonal antibodies can be prepared using standard methods known in the art (Kohler et al., 1975).

As used herein, the terms "biotin" and "biotin-related" include any molecule comprising biotin activity, i.e., ability to bind with high affinity to avidin or an avidin-related molecule (e.g., streptavidin). Examples of biotin molecules contemplated within the scope of the invention include:

Biotin:

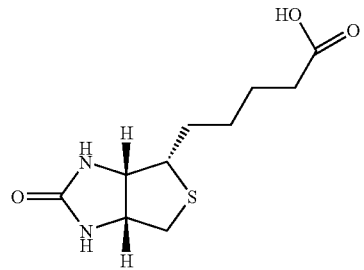

Biotin N-Hydroxysuccinimidyl Ester:

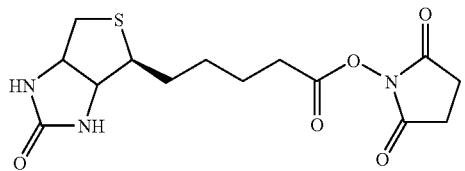

Biotinyl-L-Lysine:

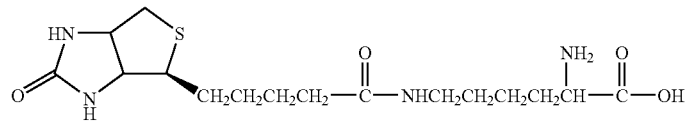

and 6-(biotinamidocaproylamido) caproic acid N-hydroxysuccinimide ester (Sigma-Aldrich, product B3295), biotinamidocaproate-N-hydroxysuccinimide ester (Sigma-Aldrich, product B2643), biotinamidocaproic acid 3-sulfo-N-hydroxysuccinimide ester (Sigma-Aldrich, product B1022) and biotin-maleimide (Sigma-Aldrich, product B1267).

Platinum complexes of the present invention are potent and selective disrupters of STAT activity. Platinum complexes of the invention can disrupt Stat3 activity and interfere with its ability to bind to its consensus binding sequence. Platinum complexes of the invention can induce cell growth inhibition and apoptosis in transformed and tumor cells with persistently active STATs. Biotin-conjugated platinum complexes of the invention can be tested for activity in suitable assays, such as MTT and XTT assays.

Methods of the invention comprise inhibiting function of a STAT by contacting a cell expressing a STAT with a platinum complex of the invention wherein the complex is taken in or otherwise provided inside the cell or on the cell membrane. Platinum complexes of the invention can physically interact with the DNA-binding domain of Stat3 and therefore disrupt its ability to bind to DNA. Alternatively, platinum complexes of the invention can interact directly with the Stat or phosphoStat monomer or dimer, reducing the activated levels of phosphorylated dimers reaching DNA. Src-transformed mouse fibroblasts, as well as human tumor cells of the breast and prostate, and mouse melanoma cells contain constitutive Stat3 activity. Platinum complexes of the invention can abrogate Stat3 signaling function and thereby induce cell growth inhibition and apoptosis.

Methods of the invention also comprise inhibiting the function and/or growth and replication of a cell that is aberrantly or constitutively expressing a STAT, such as Stat1, Stat3, or Stat5. In one embodiment, the method comprises contacting a cell with a platinum complex of the invention. In one embodiment, the cell is a tumor cell, cancer cell, or a transformed cell. The cell can be a cell from a mammal, including human, monkey, chimpanzee, ape, dog, cat, cow, pig, and horse.

Platinum complexes of the invention can be delivered to a cell either through direct contact with the cell or via a carrier means. Carrier means for delivering compositions to cells are known in the art and include, for example, encapsulating the composition in a liposome moiety. Another means for delivery of platinum complexes of the invention to a cell comprises attaching the platinum complexes to a protein or nucleic acid that is targeted for delivery to the target cell. U.S. Pat. No. 6,960,648 and Published U.S. Patent Application Nos. 20030032594 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Platinum complexes can also be incorporated into polymers, examples of which include poly(D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

The subject invention also concerns methods for treating oncological or inflammatory disorders in a patient. In one embodiment, an effective amount of a platinum complex of the present invention is administered to a patient having an oncological or inflammatory disorder and who is in need of treatment thereof. Methods of the invention can optionally include identifying a patient who is or may be in need of treatment of an oncological or inflammatory disorder. The patient can be a human or other mammal, such as a primate (monkey, chimpanzee, ape, etc.), dog, cat, cow, pig, or horse, or other animals having an oncological disorder. Means for administering and formulating platinum complexes for administration to a patient are known in the art, examples of which are described herein. Oncological disorders include cancer and/or tumors of the bone, breast, kidney, mouth, larynx, esophagus, stomach, testis, cervix, head, neck, colon, ovary, lung, bladder, skin (e.g., melanoma), liver, muscle, pancreas, prostate, blood cells (including lymphocytes), and brain. Inflammatory disorders include arthritis, multiple sclerosis, lupus, Crohn's disease, psoriasis, fibromyalgia, Alzheimer's disease, and related neurological and inflammatory connective tissue diseases (e.g., Sjögren's syndrome).

For the treatment of oncological disorders, the platinum complexes of this invention can be administered to a patient in need of treatment in combination with other antitumor or anticancer substances or with radiation and/or photodynamic therapy or with surgical treatment to remove a tumor. These other substances or radiation treatments may be given at the same as or at different times from the platinum complexes of this invention. For example, the platinum complexes of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The platinum complexes of the subject invention can be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The platinum complexes of the subject invention can also be used in combination with viral based treatments of oncologic disease. For example, platinum complexes of the invention can be used with mutant herpes simplex virus in the treatment of non-small cell lung cancer (Toyoizumi et al., 1999).

The subject invention also concerns methods for treating bacterial and viral infections of a patient using a platinum complex of the invention. In one embodiment, an effective amount of a platinum complex of the invention is administered to a patient having a bacterial or viral infection. Methods of the invention can optionally include identifying a patient who is or may be in need of treatment of a bacterial or viral infection. The patient can be a human or other mammal, such as a primate (monkey, chimpanzee, ape, etc.), dog, cat, cow, pig, or horse, or other animal infected with a bacteria or virus. Bacterial infections that can be treated according to the present invention include those from *Staphylococcus, Streptococcus, Salmonella, Bacillus, Clostridium, Pseudomonas, Neisseria, Mycobacterium*, and *Yersinia*. Viral infections that can be treated according to the present invention include, but are not limited to, those associated with human immunodeficiency virus (HIV), human T cell leukemia virus (HTLV), Papillomavirus (e.g., human papilloma virus), Polyomavirus (e.g., SV40, BK virus, DAR virus), orthopoxvirus (e.g., variola major virus (smallpox virus)), EBV, herpes simplex virus (HSV), hepatitis virus, Rhabdovirus (e.g., Ebola virus) and cytomegalovirus (CMV). Platinum compositions of the present invention can also be used to treat viral diseases in the presence of photodynamic therapy (Cuny et al., 1999). It is contemplated that these complexes are activated by light to enhance their antiviral, antibacterial, antitumor, antiparasitic, or cellular effects.

Platinum complexes of the subject invention can also be used to treat patients infected with a parasitic organism. In one embodiment, the patient is administered a therapeutically effective amount of a platinum complex of the present invention. Methods of the invention can optionally include identifying a patient who is or may be in need of treatment of a parasitic infection. The patient can be a human or other mammal, such as a primate (monkey, chimpanzee, ape, etc.), dog, cat, cow, pig, or horse, or other animal infected with a parasitic organism. Disease conditions that can be treated according to the present invention include, but are not limited to, leishmania, toxoplasmosis, schistosomiasis, trypanosomiasis, pneumocystis, malaria, and trichinosis. Parasitic organisms that can cause disease conditions treatable according to the present invention include, but are not limited to, *Leishmania, Toxoplasma, Schistosoma, Plasmodium*, and *Trypanosoma*. The subject invention can also be used to treat gastrointestinal disorders caused by parasitic organisms such as, *Entamoeba, Giardia, Trichomonas*, and nematodes such as *Ascaris, Trichuris, Enterobius, Necator, Ancylostoma, Strongyloides*, and *Trichinella*. In another embodiment, a platinum complex of the present invention can be administered to patients prophylactically, wherein an uninfected patient is traveling to or will be present in an area where parasitic disease is prevalent or poses a risk to the patient. Accordingly, the patient can be treated with a composition of the present invention prior to the patient's exposure to or presence in the area where parasitic disease is prevalent or poses a risk and/or prior to infection with the parasitic organism.

Platinum complexes of the present invention can also be used to treat biological products in vitro that are contaminated with or suspected of being contaminated with a virus on a bacterial or parasitic organism. Biological products which can be treated with a platinum complexes of the present invention include, but are not limited to, whole blood, fractionated blood, plasma, serum, whole organs, or parts of organs, and cells, including blood cells, muscle cells, skin cells, and neural cells, and products derived from cells. Products derived from cells which can be treated with a platinum complex of the present invention include, but are not limited to, interferons, interleukins, blood clotting factors such as factor VIII, IX, X, and the like, insulin, polyclonal and monoclonal antibodies, growth factors, cytokines, and other products. Treatment of biological products comprises contacting the product for an effective amount of time and with an effective amount of a platinum complex of the present invention. If necessary, the biological product can be subsequently washed, preferably with a suitable sterile wash solution such as phosphate buffered saline, to remove the platinum complex that was used to treat the product.

Therapeutic application of the subject platinum complexes, and compositions containing them, can be accomplished by any suitable therapeutic method and technique presently or prospectively known to those skilled in the art. The subject platinum complexes can be administered by any suitable route known in the art including, for example, oral, nasal (e.g., via aerosol inhalent), rectal, and parenteral routes of administration. As used herein, the term parenteral includes topical, subdermal (e.g., as in an implant), subcutaneous, intradermal, intravenous, intramuscular, intraperitoneal, and intrasternal administration, such as by injection. Administration of the subject platinum complexes of the invention can be continuous or at distinct intervals as can be readily determined by a person skilled in the art.

Platinum complexes of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive platinum complex is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, aerosol particle, and sprays. The preferred form depends on the intended mode of administration and therapeutic application. The compositions also preferably include conventional pharmaceutically acceptable carriers and diluents which are known to those skilled in the art. Examples of carriers or diluents for use with the subject platinum complexes include ethanol, ethyl acetate, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more of the subject platinum complexes based on the weight of the total composition including carrier or diluent.

The platinum complexes of the subject invention can also be administered utilizing liposome technology, slow release capsules, implantable pumps, and biodegradable containers. These delivery methods can, advantageously, provide a uniform dosage over an extended period of time. The platinum complexes of the present invention can also be administered in their salt derivative forms or crystalline forms known to those of ordinary skill in the art.

The subject invention also concerns a packaged dosage formulation comprising in one or more containers at least one platinum compound of the subject invention formulated in a pharmaceutically acceptable dosage.

All patents, patent applications, provisional applications, and publications referred to or cited herein are incorporated by reference in their entirety, including all figures and tables, to the extent they are not inconsistent with the explicit teachings of this specification.

Synthesis of NitroPlatinum (IV) Complexes.

Using 0.300 grams of Cisplatin (0.00100 moles, FW=300.1) or transplatin, 150 mL of ultra deionized water and 50 mL of dichloroethane are added to a 250-mL Erlenmeyer flask. However, hexane or any organic solvents can be substituted in place of the dichloroethane used here. Cis-diaminoplatinum(II) dichloride (cisplatin) can be purchased at 99.9% purity from Sigma-Aldrich (Product No. 4394). Trans-platinum (II) diamine dichloride (transplatin) can be purchased from Sigma-Aldrich (Product No. 1525). The choice of a sixth ligand includes the availability of a nitrogen, sulfur or oxygen atom in the chemical structure providing a Lewis base for bonding to the oxidized Pt. Biotin or biotin-lysine can be the ligand conjugated to the platinum complex by $NO_2$ gas through formation of a metal-covalent bond to Pt through the sulfur atom. Other bondings are possible with metals, halides (such as $Cl^-$) or through chelation or interaction with pi molecular orbitals. One mole of the chosen ligand per mole of cisplatin should be weighed and added to the mixture. Organic solvents, such as dichloroethane, provide solubility for organic ligands of hydrophobic nature. A magnetic stir bar is placed in the mixture and the flask placed on a magnetic stir plate in a chemical fume hood. A lecture bottle of dinitrogen tetroxide is fitted with a regulator and Teflon hose, with a glass pipet attached to the hose outlet. The pipet tip is inserted into the lower solvent (e.g., dichloroethane) and the lecture bottle warmed slightly with a warm water bath. Nitrogen dioxide gas is released at a rate of approximately one bubble per second into the stirring mixture. The gas should be added until all the yellow cisplatin is consumed; the disappearance of yellow solids and yellow solution will indicate consumption of the available cisplatin. A blue color is noted to indicate formation of the nitrosyl intermediate; variations in hue and duration of this color have been observed. Gas addition is then terminated (remove the pipet to prevent vacuum suction into the lecture bottle) and the flask covered in aluminum foil to prevent light exposure. The flask should be left to stir overnight.

Additional nitrogen dioxide may be added the next day to check for completeness of reaction. A blue color would indicate continuing reaction and incomplete oxidation of platinum (II). Normally, this blue fades within ten minutes. For a colorless ligand, the solution has become yellow overnight. If blue color remains, allow it to continue stirring. The mixture requires air for complete oxidation, so should not be tightly covered. Continued oxidation with air can be accelerated using air blown through a trap into the Erlenmeyer, over the liquids. The solvents will evaporate in about two days, leaving a yellow-orange precipitate, which is the product.

The precipitate can be purified via recrystallization in methanol, DMSO, or other suitable solvent. Alternatively, the product can be purified on silica columns or using HPLC.

To conjugate an antibody or other protein to biotin, dissolve 0.3 moles of the biotin diaminedichloronitro Pt(IV) complex in 1 mL DMSO. The antibody or protein should be prepared by measuring 0.3 moles antibody (or protein) into a buffer solution of 100 mM bicarbonate at pH 8.4 to a concentration of about 1.5-4 mg antibody (protein)/mL. Add the platinum-DMSO solution to this protein solution, wrap in foil and rotate gently at room temperature for about 4 hours. Separate product using a Sephadex G-25M column with mobile phase of 10 mM Tris, 150 mM NaCl, 0.1% $NaN_3$, pH 8.2.

MTT Assay.

1. Prepare a suspension of A549 cells or other appropriate target cells (e.g., a cell expressing an antigen recognized by an antibody bound to a biotin platinum complex of the invention) at $2 \times 10^5$ cells per mL in supplemented DMEM/F12 growth medium.
2. Plate $2 \times 10^4$ cells per well in a 96 well cell culture plate by adding 100 µL of stock suspension to each well.
3. For each platinum compound (already in solution), prepare a readily usable stock solution in DMEM/F12 medium.
4. For each compound generate triplicate trials of 0, 10, 20, 30, 40, 50, 60, and 70 µM concentration. This is achieved in situ by adding appropriate volumes of stock solution to each well along with the volume of untreated medium necessary to generate the desired concentration in a final volume of 200 µL.
5. Gently agitate plates to mix contents. Incubate at 37° C., 7% $CO_2$ for 45 hours.
6. Add 20 µL of 5 mg/mL MTT solution (in PBS) to each well.
7. Gently agitate plates to mix contents and incubate an additional 3 hours to allow product development.
8. Remove plates from incubator and agitate to cause settling of formazan product.
9. Aspirate out liquid contents of each well using needle and syringe and discard.
10. Add 200 µL DMSO to each well to dissolve formazan product.
11. Agitate plates until all of the formazan product is in solution and no purple crystals remain on the bottom surface of the wells.
12. Read the absorbance of each well at 475 nm using Varian software for Cary 50 UV-vis Spectrophotometer with fiber optic probe accessory.

XTT Assay.

A 96-well plate is used for the assays. Approximately $2.5 \times 10^4$ target cells in log phase are added to each well. A platinum complex of the invention is dispensed into each well (dissolved in 20% DMSO and 80% media), with additional media added as needed to account for uniform volumes. Control wells contain only cells and media. Each concentration assay can be performed in triplicate. Plates are incubated for 48 hours at 37° C. with 7.5% $CO_2$. XTT from MD Biosciences, Quebec, is then added according to the provided protocol concentrations and allowed to react for 3 hours. Plates are agitated 5 minutes before reading absorbance at 475 nm on a Varian Cary 50 spectrophotometer with a fibre-optic probe. Percent survival as compared to control wells is plotted against platinum complex concentration.

All percentages are by weight and all solvent mixture proportions are by volume unless otherwise noted.

TABLE 1
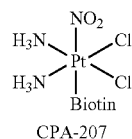
CPA-207
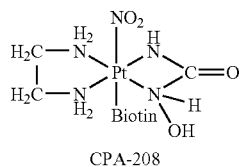
CPA-208
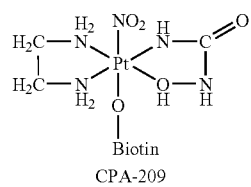
CPA-209
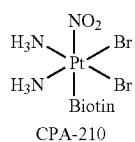
CPA-210
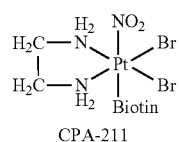
CPA-211
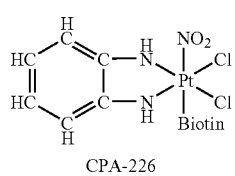
CPA-226
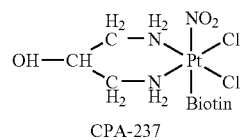
CPA-237
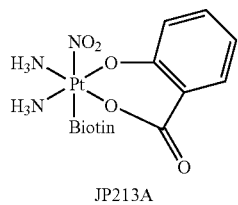
JP213A
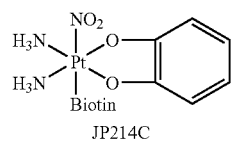
JP214C
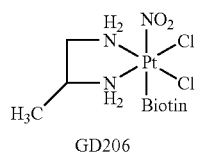
GD206
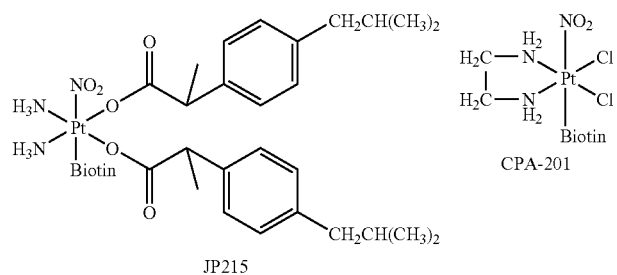
JP215
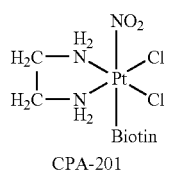
CPA-201
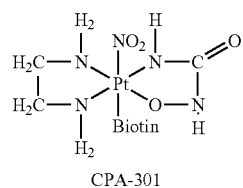
CPA-301
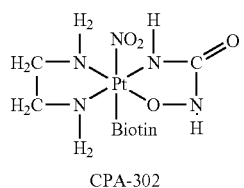
CPA-302

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 5,530,101
U.S. Pat. No. 5,585,089
U.S. Pat. No. 5,693,762
U.S. Pat. No. 6,180,370
U.S. Pat. No. 6,407,213
U.S. Pat. No. 6,690,648
Published U.S. Patent Application No. 20030032594
Published U.S. Patent Application No. 20020035243
Akira, S. (2000) "Roles of STAT3 defined by tissue-specific gene targeting" *Oncogene* 19:2607-2611.
Ardizzoni, A., Antonelli, G., Grossi, F., Tixi, L., Cafferata, M., Rosso, R. (1999) "The combination of etoposide and cisplatin in non-small-cell lung cancer (NSCLC)" *Ann. Oncol.* 10:S13-17.
Bowman, T., Garcia, R., Turkson, J., Jove, R. (2000) "STATs in oncogenesis" *Oncogene* 19:2474-2488.
Bromberg, J. F., Horvath, C. M., Wen, Z., Schreiber, R. D., Darnell, J. E., Jr. (1996) "Transcriptionally active Stat1 is required for the antiproliferative effects of both interferon alpha and interferon gamma" *Proc. Natl. Acad. Sci. USA* 93:7673-7678.
Bromberg, J. F., Horvath, C. M., Besser, D., Lathem, W. W., Darnell, J. E., Jr. (1998) "Stat3 activation is required for cellular transformation by v-src" *Mol. Cell. Biol.* 18:2553-2558.
Bromberg, J. F., Wrzeszczynska, M. H., Devgan, G., Zhao, Y., Pestell, R. G., Albanese, C., Darnell, J. E., Jr. (1999) "Stat3 as an oncogene" *Cell* 98:295-303.
Catlett-Falcone, R., Landowski, T. H., Oshiro, M. M., Turkson, J., Levitzki, A., Savino, R., Ciliberto, G., Moscinski, L., Fernandez-Luna, J. L., Nunez, G., Dalton, W. S., Jove, R. (1999a) "Constitutive activation of Stat3 signaling confers resistance to apoptosis inhuman U266 myeloma cells" *Immunity* 10:105-115.
Catlett-Falcone, R., Dalton, W. S., Jove, R. (1999b) "STAT proteins as novel targets for cancer therapy. Signal transducer an activator of transcription" *Curr. Opin. Oncol.* 11:490-496.
Coffer, P. J., Koenderman, L., de Groot, R. P. (2000) "The role of STATs in myeloid differentiation and leukemia" *Oncogene* 19:2511-2522.
Cuny, G. D. et al. (1999) "Photoactivated virucidal properties of tridentate 2,2'-dihydroxyazobenzene and 2-salicylideneaminophenol platinum pyridine complexes" *Bioorganic and Medicinal Chemistry Letters* 9(2):237-240.
Darnell, J. E., Jr., Kerr, I. M., Stark, G. R. (1994) "Jak-STAT pathways and transcriptional activation in response to IFNs and other extracellular signaling proteins" *Science* 264:1415-1421.
Darnell, J. E., Jr. (1997) "STATs and Gene Regulation" *Science* 277:1630-1635.
Epling-Burnette, P. K., Lui, J. H., Catlette-Falcone, R., Turkson, J., Oshiro, M., Kothapalli, R., Li, Y., Wang, J.-M., Yang-Yen, H.-F., Karras, J., Jove, R., Loughran, T. P., Jr. (2001) "Inhibition of STAT3 signaling leads to apoptosis of leukemic large granular lymphocytes and decreased Mcl-1 expression" *J. Clin. Invest* 107:351-362.
Fukada, T., Hibi, M., Yamanaka, Y., Takahashi-Tezuka, M., Fujitani, Y., Yamaguchi, T., Nakajima, K., Hirano, T. (1996) "Two signals are necessary for cell proliferation induced by a cytokine receptor gp130: involvement of STAT3 in anti-apoptosis" *Immunity* 5:449-460.
Garcia, R., Jove, R. (1998) "Activation of STAT transcription factors in oncogenic tyrosine kinase signaling" *J. Biomed. Sci.* 5:79-85.
Garcia, R., Bowman, T. L., Niu, G., Yu, H., Minton, S., Muro-Cacho, C. A., Cox, C. E., Falcone, R., Fairclough, R., Parson, S., Laudano, A., Gazit, A., Levitzki, A., Kraker, A., Jove, R. (2001) "Constitutive activation of Stat3 by the Src and JAK tyrosine kinases participates in growth regulation of human breast carcinoma cells" *Oncogene* 20:2499-2513.
Grandis, J. R., Drenning, S. D., Chakraborty, A., Zhou, M. Y., Zeng, Q., Pitt, A. S., Tweardy, D. J. (1998) "Requirement of Stat3 but not Stat1 activation for epidermal growth factor receptor-mediated cell growth In vitro" *J. Clin. Invest.* 102:1385-1392.
Grandis, J. R., Drenning, S. D., Zeng, Q., Watkins, S. C., Melhem, M. F., Endo, S., Johnson, D. E., Huang, L., He, Y., Kim, J. D. (2000) "Constitutive activation of Stat3 signaling abrogates apoptosis in squamous cell carcinogenesis in vivo" *Proc. Natl. Acad. Sci. USA* 97:4227-4232.
Hirano, T., Ishihara, K., Hibi, M. (2000) "Roles of STAT3 in mediating the cell growth, differentiation and survival signals relayed through the IL-6 family of cytokine receptors" *Oncogene* 19:2548-2556.
Kohler, G., C. Milstein (1975) "Continuous cultures of fused cells secreting antibody of predefined specificity" *Nature* 256(5517):495-497.
Kotenko, S. V., Pestka, S. (2000) "Jak-Stat signal transduction pathway through the eyes of cytokine class II receptor complexes" *Oncogene* 19:2557-2565.
Lin, T. S., Mahajan, S., Frank, D. A. (2000) "STAT signaling in the pathogenesis and treatment of leukemias" *Oncogene* 19:2496-2504.
Nielsen, M., Kaltoft, K., Nordahl, M., Ropke, C., Geisler, C., Mustelin, T., Dobson, P., Svejgaard, A., Odum, N. (1997) "Constitutive activation of a slowly migrating isoform of Stat3 in mycosis fungoides: tyrphostin AG490 inhibits Stat3 activation and growth of mycosis fungoides tumor cell lines" *Proc. Natl. Acad. Sci. USA* 94:6764-6769.
Nielsen, M., Kaestel, C. G., Eriksen, K. W., Woetmann, A., Stokkedal, T., Kaltoft, K., Geisler, C., Ropke, C., Odum, N. (1999) "Inhibition of constitutively activated Stat3 correlates with altered Bcl-2/Bax expression and induction of apoptosis in mycosis fungoides tumor cells" *Leukemia* 13:735-738.
Nitiss, J. L. (2002) "A copper connection to the uptake of platinum anticancer drugs" *Proc. Natl. Acad. Sci. USA* 99:13963-13965.
Persons, D. L., Yazlovitskaya, E. M., Cui, W., Pelling, J. C. (1999) "Cisplatin-induced Activation of Mitogen-activated Protein Kinases in Ovarian Carcinoma Cells: Inhibition of Extracellular Signal-regulated Kinase Activity Increases Sensitivity to Cisplatin" *Clin. Cancer Res.* 5:1007-1014.
Sanchez-Perez, I., Murguia, J. R., Perona, R. (1998) "Cisplatin induces a persistent activation of JNK that is related to cell death" *Oncogene* 16:533-540.
Schindler, C., Darnell, J. E., Jr. (1995) "Transcriptional responses to polypeptide ligands: the JAK-STAT pathway" *Annu. Rev. Biochem.* 64:621-651.

Smithgall, T. E., Briggs, S. D., Schreiner, S., Lerner, E. C., Cheng, H., Wilson, M. B. (2000) "Control of myeloid differentiation and survival by Stats" *Oncogene* 19:2612-2618.

Song, J. I., Grandis, J. R. (2000) "STAT signaling in head and neck cancer" *Oncogene* 19:2489-2495.

Stark, G. R., Kerr, I. M., Williams, B. R., Silverman, R. H., Schreiber, R. D. (1998) "How cells respond to interferons" *Annu. Rev. Biochem.* 67:227-264.

Toyoizumi, T., R. Mick, A. E. Abbas, E. H. Kang, L. R. Kaiser, K. L. Molnar-Kimber (1999) "Combined therapy with chemotherapeutic agents and herpes simplex virus type IICP34.5 mutant (HSV-1716) in human non-small cell lung cancer" *Human Gene Therapy* 10(18):17.

Turkson, J., Bowman, T., Garcia, R., Caldenhoven, E., de Groot, R. P., Jove, R. (1998) "Stat3 activation by Src induces specific gene regulation and is required for cell transformation" *Mol. Cell. Biol.* 18:2545-2552.

Turkson, J., Jove, R. (2000) "STAT proteins: novel molecular targets for cancer drug discovery" *Oncogene* 19:6613-6626.

I claim:

1. A platinum complex having the structure shown in formula I or II:

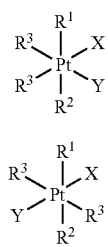

wherein

X and Y are, independently, any halogen, —NO$_2$, —ONO, or the structure:

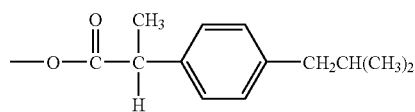

or X and Y together form the structure:

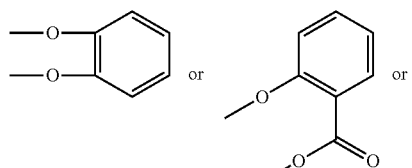

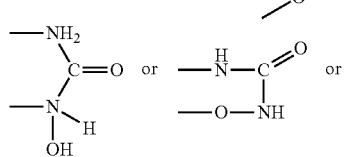

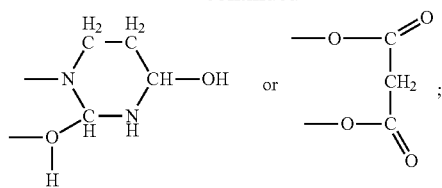

$R^1$ is —NO$_2$, —ONO, —OH, Cl, Br, I, or F;

$R^2$ is a biotin-containing molecule;

$R^3$ is independently, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, hetero aryloxycarbonyl, heterocycloalkoxy, or heterocycloalkoxycarbonyl, any of which can be optionally substituted with any halogen, —COOH, —OH, —NO$_2$, —NH$_2$, —NH$_3$, —NHR$^7$, NH$_2$R$^7$, —NH(R$^7$)$_2$, —N(R$^7$)$_3$—N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; and $R^7$ is H, C$_{1-6}$ alkyl, alkoxy, or aryl, any of which can be optionally substituted with any halogen, —NO$_2$, or —COOH;

or a pharmaceutically acceptable salt thereof.

2. The platinum complex according to claim 1, wherein X and Y are, independently, selected from the group consisting of F, Cl, Br, and I.

3. The platinum complex according to claim 1, wherein X and Y are both Cl or X and Y are both Br.

4. The platinum complex according to claim 1, wherein $R^1$ is —NO$_2$.

5. The platinum complex according to claim 1, wherein $R^3$ is —NH$_3$.

6. A platinum complex having the structure shown in formula III:

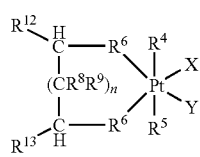

wherein

X and Y are, independently, any halogen, or the structure:

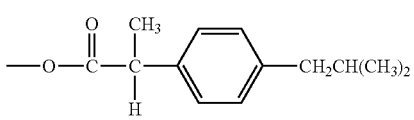

or X and Y together form the structure:

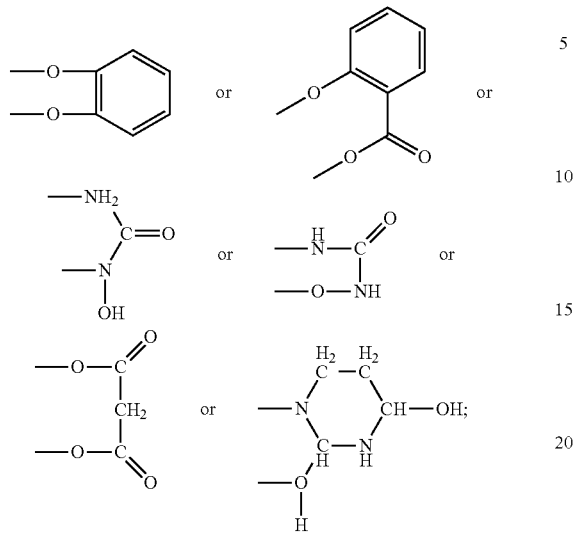

R⁴ is —NO₂, —ONO, —OH, Cl, Br, or F;

R⁵ is a biotin-containing molecule;

R⁶ is, independently, NH₂, NH, NHR⁷, N(R⁷)₂, NHR⁸, N(R⁸)₂, NHR⁹, N(R⁹)₂, or NR⁸R⁹;

R⁷ is H, $C_{1-6}$ alkyl, alkoxy, or aryl, any of which can be optionally substituted with any halogen, —NO₂, or —COOH;

R⁸ and R⁹ are, independently, H, $C_{1-6}$ alkyl, or —OH, any of which can be optionally substituted with any halogen, —COOH, —OH, —NO₂, —NH₂, alkyl, alkoxy, cycloalkyl, cycloalkoxy, aryl, aryloxy, alkycarbonyl, alkoxycarbonyl, cycloalkylcarbonyl, heteroalkyl, heterocycloalkyll, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

R¹² and R¹³ are, independently, H or $C_{1-6}$ alkyl, or R¹² and R¹³ together form an aryl, cycloalkyl, heterocycloalkyl, or heteroaryl, any of which can be optionally substituted with any halogen, —COOH, —OH, —NO₂, —NH₂, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, aryl carbonyl, heteroarylcarbonyl, aryloxycarbonyl, heteroaryloxycarbonyl, heterocycloalkoxy, or heterocycloalkoxycarbonyl; and n is any integer from 0 to 6;

or a pharmaceutically acceptable salt thereof.

7. The platinum complex according to claim 6, wherein X and Y are, independently, selected from the group consisting of F, Cl, Br, and I.

8. The platinum complex according to claim 6, wherein X and Y are both Cl or X and Y are both Br.

9. The platinum complex according to claim 6, wherein R⁴ is —NO₂.

10. The platinum complex according to claim 6, wherein R⁶ is —NH₂.

11. A platinum complex having the structure shown in formula IV, VA, or VB:

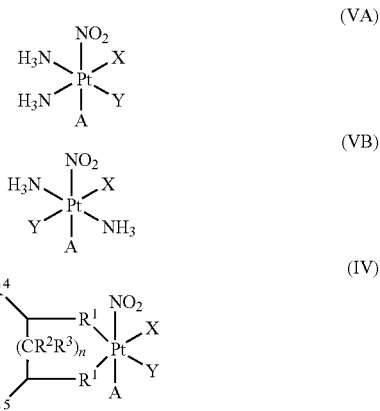

wherein
X and Y are, independently, any halogen, —OH, H₂O, or —SO(CH₃)₂;
or X and Y together form the structure:

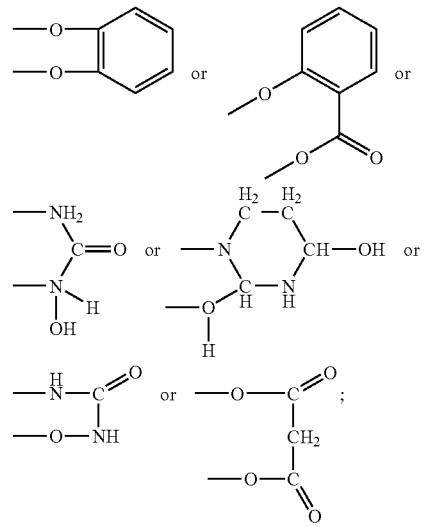

A is a biotin-containing molecule;
R¹ is, independently, NH₂, NH, NR⁴, NHR⁴, N(R⁴)₂, NR⁵, NHR⁵, N(R⁵)₂, or NR⁴R⁵;
R² and R³ are, independently, H, —OH, $C_{1-6}$ alkyl, alkoxy, cycloalkyl, aryloxy, cycloalkoxy, aryl, heteroalkyl, heterocycloalkyl, heteroaryl, arylcarbonyl, or heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl;
R⁴ and R⁵ are, independently, H or $C_{1-6}$ alkyl, alkoxy, cycloalkyl, aryloxy, cycloalkoxy, aryl, heteroalkyl, heterocycloalkyl, heteroaryl, arylcarbonyl, and heteroarylcarbonyl or R⁴ and R⁵ together form a cycloalkyl, cycloalkoxy, aryl, aryloxy, heterocycloalkyl, heteroaryl, arylcarbonyl, or heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl; and n is any integer from 0 to 6;
or a pharmaceutically acceptable salt thereof.

12. The platinum complex according to claim 11, wherein X and Y are, independently, selected from the group consisting of F, Cl, Br, and I.

13. The platinum complex according to claim 11, wherein X and Y are both Cl.

14. A method for treating an oncological disorder in a patient, said method comprising administering an effective amount of a platinum complex, wherein said platinum complex has the structure shown in a) formula I or II:

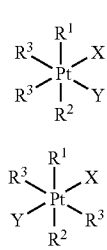

(I)

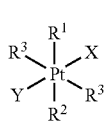

(II)

wherein
X and Y are, independently, any halogen, —NO$_2$, —ONO, or the structure:

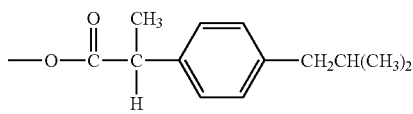

or X and Y together form the structure:

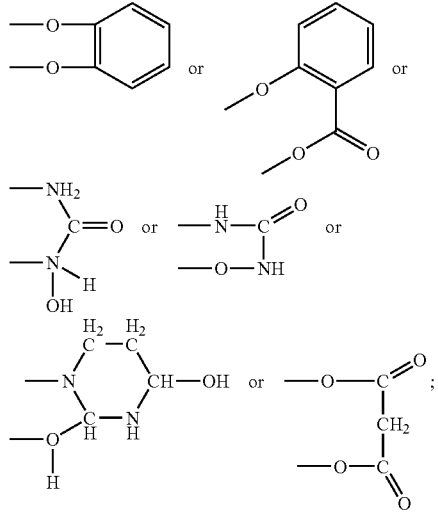

$R^1$ is —NO$_2$, —ONO, —OH, Cl, Br, I, or F;
$R^2$ is a biotin-containing molecule;
$R^3$ is independently, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —NO$_2$, —NH$_2$, —NH$_3$, —NHR$^7$, NH$_2$R$^7$, —NH(R$^7$)$_2$, —N(R$^7$)$_3$—N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; and
$R^7$ is H, C$_{1-6}$ alkyl, alkoxy, or aryl, any of which can be optionally substituted with any halogen, —NO$_2$, or —COOH; or
b) the structure shown in formula III:

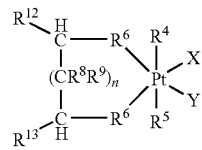

(III)

wherein
X and Y are, independently, any halogen, or the structure:

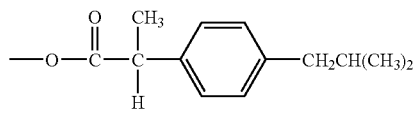

or X and Y together form the structure:

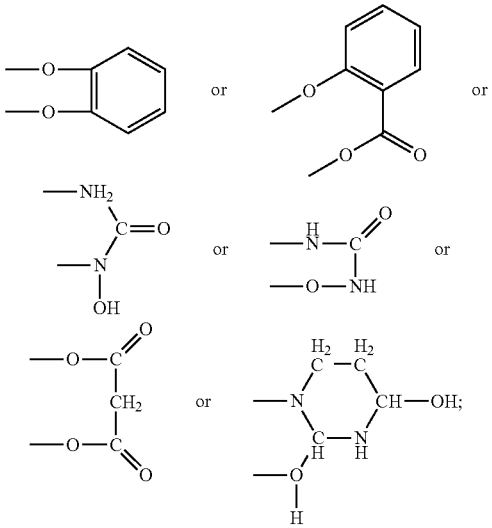

$R^4$ is —NO$_2$, —ONO, —OH, Cl, Br, or F;
$R^5$ is a biotin-containing molecule;
$R^6$ is, independently, NH$_2$, NH, NHR$^7$, N(R$^7$)$_2$, NHR$^8$, N(R$^8$)$_2$, NHR$^9$, N(R$^9$)$_2$, or NR$^8$R$^9$;
$R^7$ is H, C$_{1-6}$ alkyl, alkoxy, or aryl, any of which can be optionally substituted with any halogen, —NO$_2$, or —COOH;
$R^8$ and $R^9$ are, independently, H, C$_{1-6}$ alkyl, or —OH, any of which can be optionally substituted with any halogen, —COOH, —OH, —NO$_2$, —NH$_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{12}$ and $R^{13}$ are, independently, H or $C_{1-6}$ alkyl, or $R^{12}$ and $R^{13}$ together form an aryl, cycloalkyl, heterocycloalkyl, or heteroaryl, any of which can be optionally substituted with any halogen, —COOH, —OH, —NO$_2$, —NH$_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; and n is any integer from 0 to 6; or c) the structure shown in formula IV, VA, or VB:

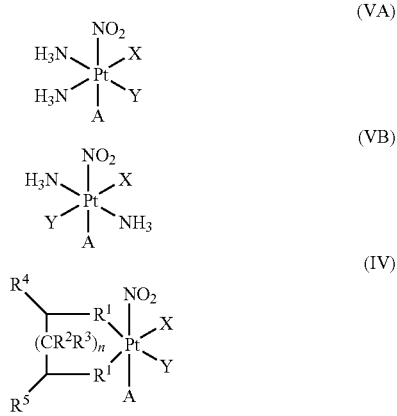

wherein
X and Y are, independently, any halogen, —OH, H$_2$O, or —SO(CH$_3$)$_2$;
or X and Y together form the structure:

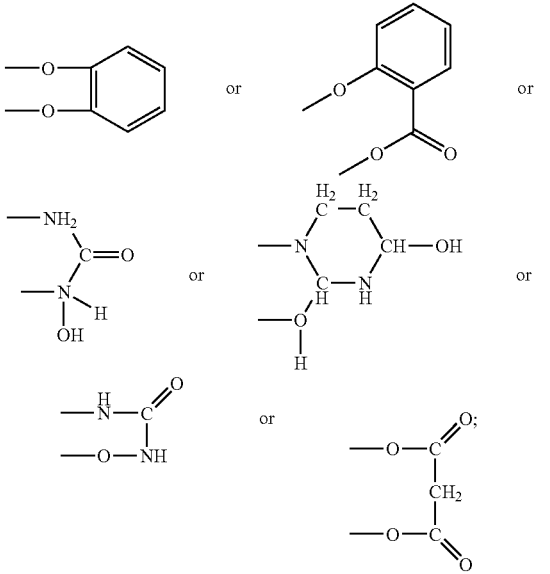

A is a biotin-containing molecule;

$R^1$ is, independently, NH$_2$, NH, NR$^4$, NHR$^4$, N(R$^4$)$_2$, NR$^5$, NHR$^5$, N(R$^5$)$_2$, or NR$^4$R$^5$;

$R^2$ and $R^3$ are, independently, H, —OH, $C_{1-6}$ alkyl, alkoxy, cycloalkyl, aryloxy, cycloalkoxy, aryl, heteroalkyl, heterocycloalkyl, heteroaryl, arylcarbonyl, or heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl;

$R^4$ and $R^5$ are, independently, H or $C_{1-6}$ alkyl, alkoxy, cycloalkyl, aryloxy, cycloalkoxy, aryl, heteroalkyl, heterocycloalkyl, heteroaryl, arylcarbonyl, and heteroarylcarbonyl or $R^4$ and $R^5$ together form a cycloalkyl, cycloalkoxy, aryl, aryloxy, heterocycloalkyl, heteroaryl, arylcarbonyl, or heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl; and n is any integer from 0 to 6;

or a pharmaceutically acceptable salt of any of the above platinum complexes.

15. The method according to claim 14, further comprising first identifying a patient having an oncological disorder.

16. The method according claim 14, wherein the patient is a human, monkey, chimpanzee, ape, dog, cat, horse, cow, or pig.

17. The method according to claim 14, wherein the oncological disorder is a cancer or tumor of bone, breast, kidney, mouth, larynx, esophagus, stomach, testis, cervix, head, neck, colon, ovary, lung, bladder, skin, liver, muscle, pancreas, prostate, blood cells, or brain.

18. The method according to claim 14, wherein the oncological disorder is melanoma.

19. The method according to claim 14, wherein said platinum complex is encapsulated in a liposome moiety or said platinum complex comprises a protein or nucleic acid that targets delivery of the platinum complex to a cell.

20. The method according to claim 14, wherein said platinum complex is administered in an amount effective to alleviate at least one symptom of the oncological disorder in the patient.

21. A method for synthesis of a platinum complex, said method comprising:
 a) mixing cisplatin or transplatin in water and an organic solvent;
 b) mixing into the mixture of step (a) a biotin containing ligand capable of bonding to the platinum of cisplatin or transplatin to form the platinum complex product;
 c) contacting the mixture of step (b) with nitrogen dioxide gas; and
 d) separating the platinum complex product from the solvent.

22. The method according to claim 21, wherein the organic solvent is dichloroethane or hexane.

23. The method according to claim 21, wherein the platinum complex product is separated from the solvent by evaporation of the solvent.

24. The method according to claim 21, wherein following step (d), the platinum complex product is further purified.

25. The method according to claim 24, wherein the platinum complex product is further purified by recrystallization in a solvent.

26. The method according to claim 24, wherein the platinum complex product is further purified by adsorption on a silica column or by high performance liquid chromatography (HPLC).

27. A method for inhibiting the function, growth, and/or replication of a cell, wherein said cell is aberrantly or constitutively expressing a STAT, wherein said method comprises contacting said cell with an effective amount of a platinum complex, wherein said platinum complex has the structure shown in a) formula I or II:

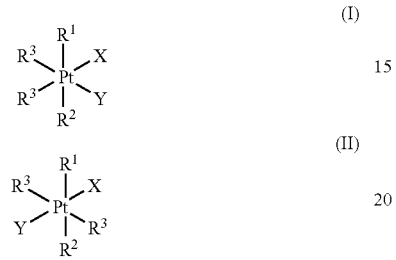

wherein
X and Y are, independently, any halogen, —$NO_2$, —ONO, or the structure:

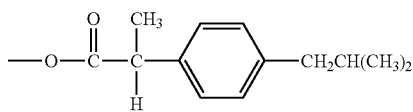

or X and Y together form the structure:

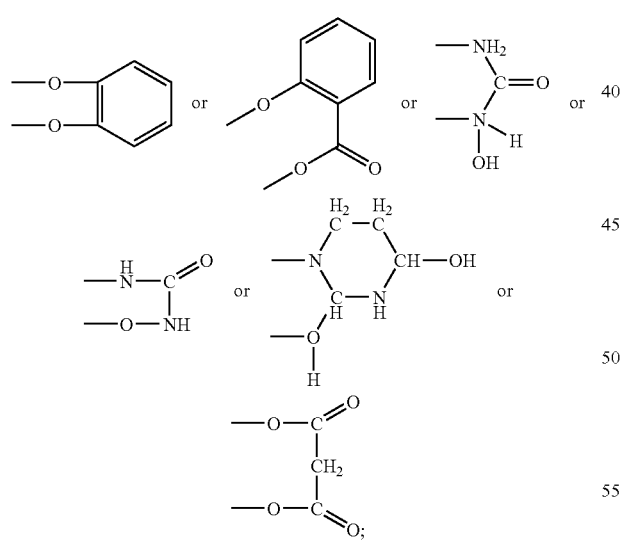

$R^1$ is —$NO_2$, —ONO, —OH, Cl, Br, I, or F;
$R^2$ is a biotin-containing molecule;
$R^3$ is independently, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —$NO_2$, —$NH_2$, —$NH_3$, —$NHR^7$, $NH_2R^7$, —$NH(R^7)_2$, —$N(R^7)_3$—N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; and
$R^7$ is H, $C_{1-6}$ alkyl, alkoxy, or aryl, any of which can be optionally substituted with any halogen, —$NO_2$, or —COOH; or b) the structure shown in formula III:

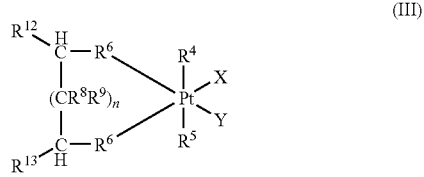

wherein
X and Y are, independently, any halogen, or the structure:

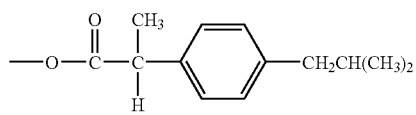

or X and Y together form the structure:

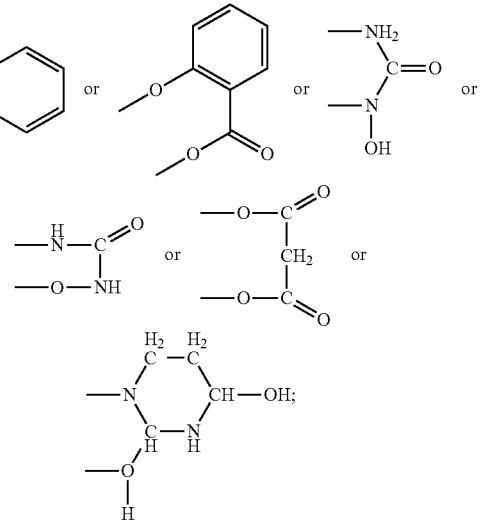

$R^4$ is —$NO_2$, —ONO, —OH, Cl, Br, or F;
$R^5$ is a biotin-containing molecule;
$R^6$ is, independently, $NH_2$, NH, $NHR^7$, $N(R^7)_2$, $NHR^8$, $N(R^8)_2$, $NHR^9$, $N(R^9)_2$, or $NR^8R^9$;
$R^7$ is H, $C_{1-6}$ alkyl, alkoxy, or aryl, any of which can be optionally substituted with any halogen, —$NO_2$, or —COOH;
$R^8$ and $R^9$ are, independently, H, $C_{1-6}$ alkyl, or —OH, any of which can be optionally substituted with any halogen, —COOH, —OH, —$NO_2$, —$NH_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{12}$ and $R^{13}$ are, independently, H or $C_{1-6}$ alkyl, or $R^{12}$ and $R^{13}$ together form an aryl, cycloalkyl, heterocycloalkyl, or heteroaryl, any of which can be optionally substituted with any halogen, —COOH, —OH, —NO$_2$, —NH$_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; and n is any integer from 0 to 6; or c) the structure shown in formula IV, VA, or VB:

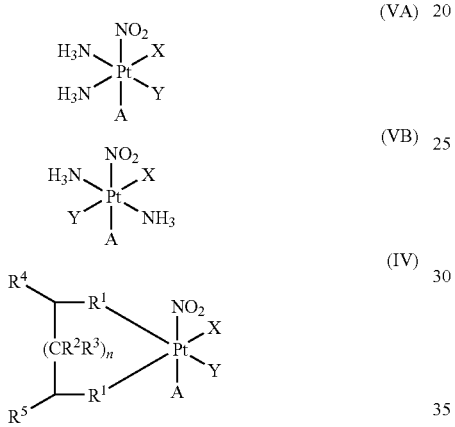

wherein
X and Y are, independently, any halogen, —OH, H$_2$O, or —SO(CH$_3$)$_2$;
or X and Y together form the structure:

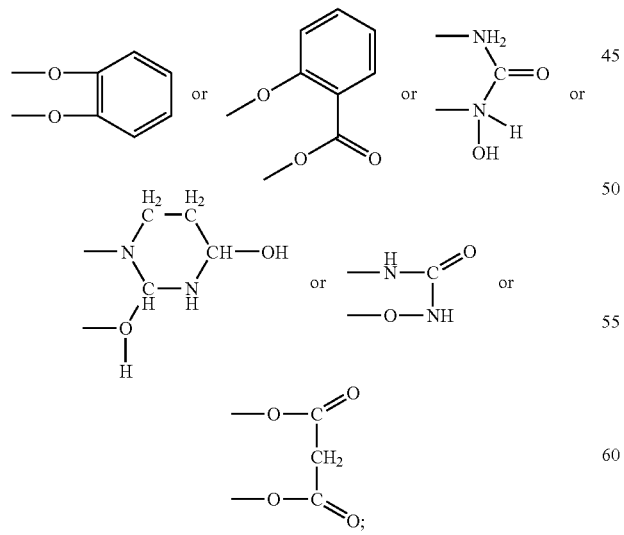

A is a biotin-containing molecule;
$R^1$ is, independently, NH$_2$, NH, NR$^4$, NHR$^4$, N(R$^4$)$_2$, NR$^5$, NHR$^5$, N(R$^5$)$_2$, or NR$^4$R$^5$;

$R^2$ and $R^3$ are, independently, H, —OH, $C_{1-6}$ alkyl, alkoxy, cycloalkyl, aryloxy, cycloalkoxy, aryl, heteroalkyl, heterocycloalkyl, heteroaryl, arylcarbonyl, or heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl;

$R^4$ and $R^5$ are, independently, H or $C_{1-6}$ alkyl, alkoxy, cycloalkyl, aryloxy, cycloalkoxy, aryl, heteroalkyl, heterocycloalkyl, heteroaryl, arylcarbonyl, and heteroarylcarbonyl or $R^4$ and $R^5$ together form a cycloalkyl, cycloalkoxy, aryl, aryloxy, heterocycloalkyl, heteroaryl, arylcarbonyl, or heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, or heteroarylcarbonyl; and n is any integer from 0 to 6;

or a pharmaceutically acceptable salt of any of the above platinum complexes.

28. The method according to claim 27, wherein said cell is a tumor cell, a cancer cell, or a transformed cell.

29. The method according to claim 27, wherein said cell is a human cell, monkey cell, chimpanzee cell, ape cell, dog cell, cat cell, cow cell, pig cell, or horse cell.

30. The platinum complex according to claim 1, wherein $R^1$ is —NO$_2$; X and Y are independently Cl or Br, or the structure

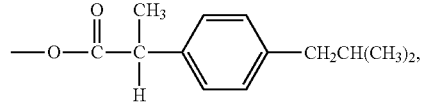

or X and Y together form the structure

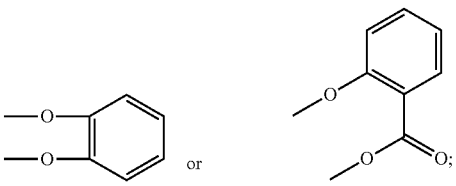

and $R^3$ is —NH$_3$.

31. The platinum complex according to claim 6, wherein $R^4$ is —NO$_2$; $R^6$ is —NH or —NH$_2$; X and Y are independently Cl or Br, or X and Y together form the structure

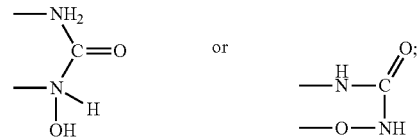

and when n is 0, $R^{12}$ is H, $R^{13}$H or CH$_3$, or $R^{12}$ and $R^{13}$ together form a benzene ring, and when n is 1, $R^{12}$ and $R^{13}$ are both H, and $R^8$ and $R^9$ are H or —OH.

32. The platinum complex according to claim 11, wherein $R^1$ is —NH or —NH$_2$, X and Y are independently CL or Br, or, X and Y together form the structure

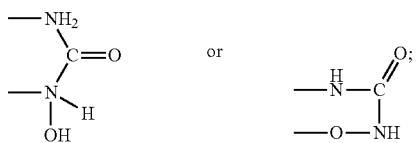 or 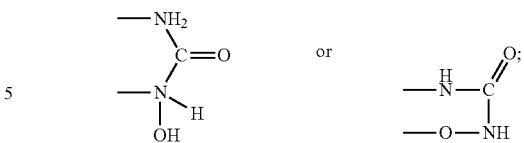

and when n is 0, $R^4$ is H, $R^5$ is H or $CH_3$, or $R^4$ and $R^5$ together form a benzene ring, and when n is 1, $R^4$ and $R^5$ are both H, and $R^2$ and $R^3$ are H or —OH.

33. The platinum complex according to claim 11, wherein X and Y are independently Cl or Br, or the structure

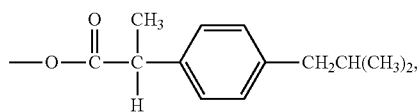

or

X and Y together form the structure

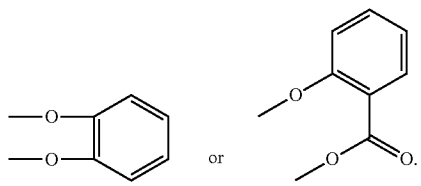

34. The method according to claim 14, wherein the platinum complex has the structure shown in formula I or II and wherein $R^1$ is —$NO_2$; X and Y are independently Cl or Br, or the structure

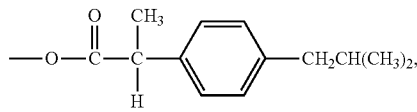

or X and Y together form the structure

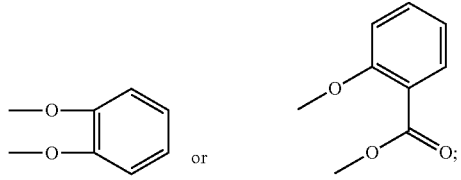

and $R^3$ is —$NH_3$.

35. The method according to claim 14, wherein the platinum complex has the structure shown in formula III and wherein $R^4$ is —$NO_2$; $R^6$ is —NH or —$NH_2$; X and Y are independently Cl or Br, or X and Y together form the structure and when n is 0, $R^{12}$ is H, $R^{13}$H or $CH_3$, or $R^{12}$ and $R^{13}$ together form a benzene ring, and when n is 1, $R^{12}$ and $R^{13}$ are both H, and $R^8$ and $R^9$ are H or —OH.

36. The method according to claim 14, wherein the platinum complex has the structure shown in formula IV and wherein $R^1$ is —NH or —$NH_2$, X and Y are independently CL or Br, or, X and Y together form the structure

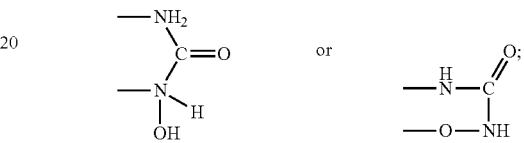

and when n is 0, $R^4$ is H, $R^5$ is H or $CH_3$, or $R^4$ and $R^5$ together form a benzene ring, and when n is 1, $R^4$ and $R^5$ are both and $R^2$ and $R^3$ are H or —OH.

37. The method according to claim 14, wherein the platinum complex has the structure shown in formula VA or VB and wherein X and Y are independently Cl or Br, or the structure

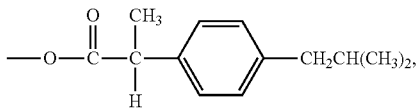

or

X and Y together form the structure

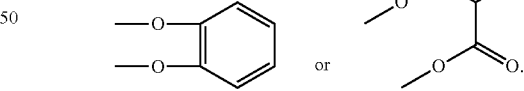

38. The method according to claim 27, wherein the platinum complex has the structure shown in formula I or II and wherein $R^1$ is —$NO_2$; X and Y are independently Cl or Br, or the structure

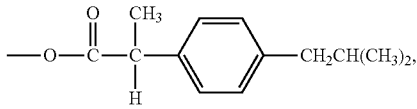

or X and Y together form the structure

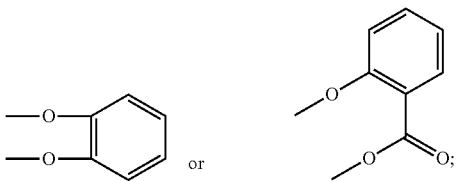 or and $R^3$ is $-NH_3$.

39. The method according to claim 27, wherein the platinum complex has the structure shown in formula III and wherein $R^4$ is $-NO_2$; $R^6$ is $-NH$ or $-NH_2$; X and Y are independently Cl or Br, or X and Y together form the structure

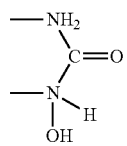 or 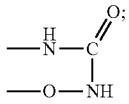

and when n is 0, $R^{12}$ is H, $R^{13}$H or $CH_3$, or $R^{12}$ and $R^{13}$ together form a benzene ring, and when n is 1, $R^{12}$ and $R^{13}$ are both H, and $R^8$ and $R^9$ are H or $-OH$.

40. The method according to claim 27, wherein the platinum complex has the structure shown in formula IV and wherein $R^1$ is $-NH$ or $-NH_2$, X and Y are independently CL or Br, or, X and Y together form the structure

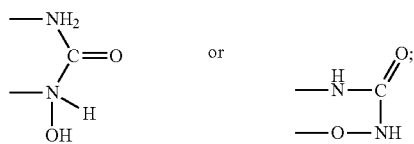

and when n is 0, $R^4$ is H, $R^5$ is H or $CH_3$, or $R^4$ and $R^5$ together form a benzene ring, and when n is 1, $R^4$ and $R^5$ are both H, and $R^2$ and $R^3$ are H or $-OH$.

41. The method according to claim 27, wherein the platinum complex has the structure shown in formula VA or VB and wherein X and Y are independently Cl or Br, or the structure

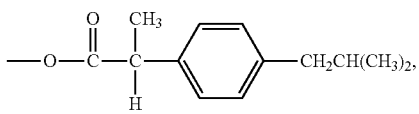

or
X and Y together form the structure

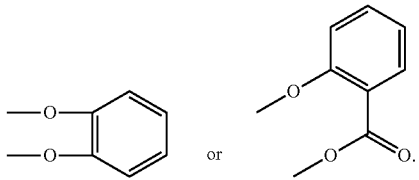

* * * * *

UNITED STATES PATENT AND TRADEMARK OFFICE
CERTIFICATE OF CORRECTION

| | | |
|---|---|---|
| PATENT NO. | : 7,977,500 B2 | Page 1 of 1 |
| APPLICATION NO. | : 11/667617 | |
| DATED | : July 12, 2011 | |
| INVENTOR(S) | : Heidi Kay | |

It is certified that error appears in the above-identified patent and that said Letters Patent is hereby corrected as shown below:

Column 9,
Line 18, "disrupters" should read --disruptors--.

Column 13,
Lines 21-22, "Cis-diaminoplatinum(II)" should read --Cis-diammineplatinum(II)--.
Line 24, "diamine" should read --diammine--.

Column 14,
Line 5, "diaminedichloronitro Pt(IV)" should read --diamminedichloronitroPt(IV)--.

Column 21,
Line 51, "aryl carbonyl" should read --arylcarbonyl--.

Column 24,
Line 2, "-COOH, -NO$_2$" should read -- -COOH, -OH, -NO$_2$--.

Column 30,
Line 66, "CL" should read --Cl--.

Column 32,
Line 15, "CL" should read --Cl--.

Column 33,
Line 34, "CL" should read --Cl--.

Signed and Sealed this
Twenty-seventh Day of December, 2011

David J. Kappos
*Director of the United States Patent and Trademark Office*